United States Patent [19]

Kawamura et al.

[11] Patent Number: 5,031,631
[45] Date of Patent: Jul. 16, 1991

[54] AUTOMATIC BLOOD PRESSURE MEASURING APPARATUS HAVING PRESSURE CHAMBER-RELIEVING MEANS

[75] Inventors: Norio Kawamura, Nagoya; Noriyuki Kaida, Kakamigahara, both of Japan

[73] Assignee: Colin Electronics Co., Ltd., Japan

[21] Appl. No.: 395,650

[22] Filed: Aug. 18, 1989

[51] Int. Cl.$^5$ .............................................. A61B 5/022
[52] U.S. Cl. ................................... 128/685; 128/686; 128/672
[58] Field of Search ................. 128/685, 686, 672, 677

[56] References Cited

U.S. PATENT DOCUMENTS

| | | | |
|---|---|---|---|
| 3,896,791 | 7/1975 | Ono | 128/686 X |
| 4,013,265 | 3/1977 | Speidel | 128/685 X |
| 4,200,259 | 4/1980 | Ueda | 128/685 X |
| 4,378,807 | 4/1983 | Peterson et al. | 128/677 |
| 4,667,672 | 5/1987 | Romanowski | 128/686 X |
| 4,690,171 | 9/1987 | Johnston | 128/685 X |

Primary Examiner—Richard J. Apley
Assistant Examiner—L. Thomas
Attorney, Agent, or Firm—Oliff & Berridge

[57] ABSTRACT

An apparatus for automatically measuring a blood pressure of a subject, including a device for defining an inflatable pressure chamber, the device being set on a body portion of the subject, a flexible piping, a device for supplying a pressurized fluid to the inflatable pressure chamber via the flexible piping so as to increase fluid pressure in the pressure chamber and thereby press the body portion of the subject, and a relief device for discharging the pressurized fluid in the inflatable pressure chamber, into atmosphere, if the fluid pressure in the pressure chamber exceeds a predetermined value, the relief means being supported by the means for defining the pressure chamber.

21 Claims, 2 Drawing Sheets

AUTOMATIC BLOOD PRESSURE MEASURING APPARATUS HAVING PRESSURE CHAMBER-RELIEVING MEANS

BACKGROUND OF THE INVENTION

1. Field of the Invention

The present invention generally relates to an automatic blood pressure (BP) measuring apparatus and particularly to such an apparatus which has an inflatable pressure chamber for pressing a body portion of a subject.

2. Discussion of the Prior Art

There is known an automatic BP measuring apparatus of the type having (a) a pressing device which has an inflatable pressure chamber and which is set around a body portion of a subject, (b) a flexible hose, (c) a supply device for supplying pressurized fluid to the inflatable pressure chamber via the flexible hose so as to increase fluid pressure in the pressure chamber and thereby press the body portion of the subject, and (d) a relief-valve device for discharging the pressurized fluid in the inflatable pressure chamber if the fluid pressure in the pressure chamber exceeds a predetermined value as the pressurized fluid is supplied to the pressure chamber.

However, in the BP measuring apparatus of the above-described type, the relief-valve device is associated with the main body of the apparatus which is spaced apart from the pressing device or inflatable pressure chamber via the flexible hose provided therebetween. Accordingly, if the flexible hose is bent double, the relief-valve device may erroneously be operated, that is, placed in its operative position in which the device permits a decrease in the fluid pressure in the inflatable pressure chamber, though the fluid pressure in the pressure chamber may not have exceeded the predetermined value. In the case where the relief-valve device is provided with a manually operated reset mechanism for restoring the device from its operative position to its inoperative position, the operator or subject must operate the reset mechanism each time the relief-valve device is changed from its inoperative position to its operative position due to bending of the flexible hose.

SUMMARY OF THE INVENTION

It is therefore an object of the present invention to provide an automatic blood pressure measuring apparatus in which the relief means for discharging the pressurized fluid in the inflatable pressure chamber, is operated with high reliability.

The above object has been achieved by the present invention, which provides an apparatus for automatically measuring a blood pressure of a subject, comprising (i) means for defining an inflatable pressure chamber, the means being set on a body portion of the subject, (ii) a flexible piping, (iii) means for supplying a pressurized fluid to the inflatable pressure chamber via the flexible piping so as to increase fluid pressure in the pressure chamber and thereby press the body portion of the subject, and (iv) relief means for discharging the pressurized fluid in the inflatable pressure chamber, into atmosphere, if the fluid pressure in the pressure chamber exceeds a predetermined value, the relief means being supported by the means for defining the pressure chamber.

In the automatic BP measuring apparatus constructed as described above, the relief means is directly associated with the inflatable pressure chamber, in constrast to the previously-indicated conventional apparatus in which the relief-valve device is disposed apart from the inflatable pressure chamber via the flexible hose provided therebetween, that is, on the upstream side of the flexible hose regarding the pressurized fluid supplied from the supply means to the pressure chamber. Therefore, the relief means of the invention apparatus is operated directly depending on the level of the fluid pressure in the inflatable pressure chamber. Consequently the present apparatus is free from the conventionally encountered problem that the relief-valve device or other relief means erroneously is operated due to bending of the flexible hose. Moreover, the present apparatus has eliminated the trouble of manually restoring the relief-valve device from the operative position to the inoperative position each time the relief-valve device erroneously is operated.

Preferably the apparatus further comprises means for detecting pulse waves produced from an artery running beneath the body portion of the subject, and means for determining a blood pressure of the subject based on the detected pulse waves.

According to a preferred feature of the present invention, the relief means comprises a cylindrical valve member formed of a rubber material, one of opposite axial ends of the cylindrical valve member being closed, while the other end of the valve member being open, the open end of the valve member communicating with the atmosphere, the valve member having at least one cut of a predetermined length which is made through the thickness of a cylindrical side wall of the valve member and extends axially of the valve member, the valve member being operated such that, while the fluid pressure in the inflatable pressure chamber is below the predetermined value, the valve member is in an inoperative condition thereof in which the at least one cut is fluid-tightly closed, and that, when the fluid pressure exceeds the predetermined value, the valve member is placed in an operative condition thereof in which the at least one cut is opened due to elastic deformation of one of a pair of lips adjacent to the at least one cut so that the pressurized fluid in the pressure chamber is discharged into the atmosphere through the opened at least one cut.

In a preferred form of the above-indicated embodiment, the means for defining the inflatable pressure chamber comprises an inflatable cuff formed of a rubber material, the cylindrical valve member being formed integral with the inflatable cuff such that the open end of the valve member is exposed to the atmosphere and the closed end thereof is located in the pressure chamber.

In another form of the same embodiment, the means for defining the inflatable pressure chamber comprises an inflatable cuff formed of a rubber material, the relief means further comprising a fixture member fluid-tightly secured to the inflatable cuff, the fixture member having a stepped cylindrical shape which includes a small-diameter portion and a large-diameter portion connected to each other at an intermediate shoulder portion thereof, the cylindrical valve member further including a large-diameter cylindrical portion which extends axially outwardly from the open end thereof and which has an outer diameter sufficiently larger than an outer diameter of a cylindrical main body of the valve member and slightly smaller than an inner diameter of the large-diameter portion of the fixture member, the valve member being press-fitted in the large-diameter portion of the fixture member such that the large-diameter cylindrical portion of the valve member is held in fluid-tight contact with the shoulder portion of the fixture member and communicates with the small-diameter portion of the fixture member, the small-diameter portion of the fixture member being exposed to the atmosphere, while the large-diameter portion of the fixture member being located in the pressure chamber.

In yet another form of the same embodiment, the at least one cut consists of a pair of opposite cuts made in the cylindrical side wall of the cylindrical valve member.

In a further form of the same embodiment, the at least one cut is opened when the fluid pressure in the inflatable pressure chamber exceeds 350 mmHg.

In a still further form of the same embodiment, the cylindrical valve member once placed in the operative condition thereof continues to be in the same condition due to radial overlapping of the pair of lips adjacent to the opened at least one cut, thereby permitting the pressurized fluid in the inflatable pressure chamber to be discharged through the opened at least one cut, even if the supply means continues to supply the pressurized fluid to the pressure chamber. In this case, the fluid pressure in the inflatable pressure chamber may be decreased down to about 20 mmHg while the cylindrical valve member continues to be in the operative condition thereof.

According to a feature of the same embodiment, the cylindrical valve member is restored from the operative position thereof to the inoperative condition thereof by blowing air into a cylindrical main body of the valve member through the open end thereof.

According to another aspect of the present invention, there is provided a pressing device for pressing a body portion of a subject, comprising (i) means for defining an inflatable pressure chamber, the means being set on the body portion of the subject, (ii) means for supplying a pressurized fluid to the inflatable pressure chamber so as to increase fluid pressure in the pressure chamber and thereby press the body portion of the living body, and (iii) relief means for discharging the pressurized fluid in the inflatable pressure chamber, into atmosphere, if the fluid pressure in the pressure chamber exceeds a predetermined value, the relief means being supported by the means for defining the pressure chamber.

BRIEF DESCRIPTION OF THE DRAWINGS

The above and optional objects, features and advantages of the present invention will be better understood by reading the detailed description of the presently preferred embodiment of the invention, when considered in conjunction with the accompanying drawings, in which.

DETAILED DESCRIPTION OF THE PREFERRED EMBODIMENT

Figure 1:
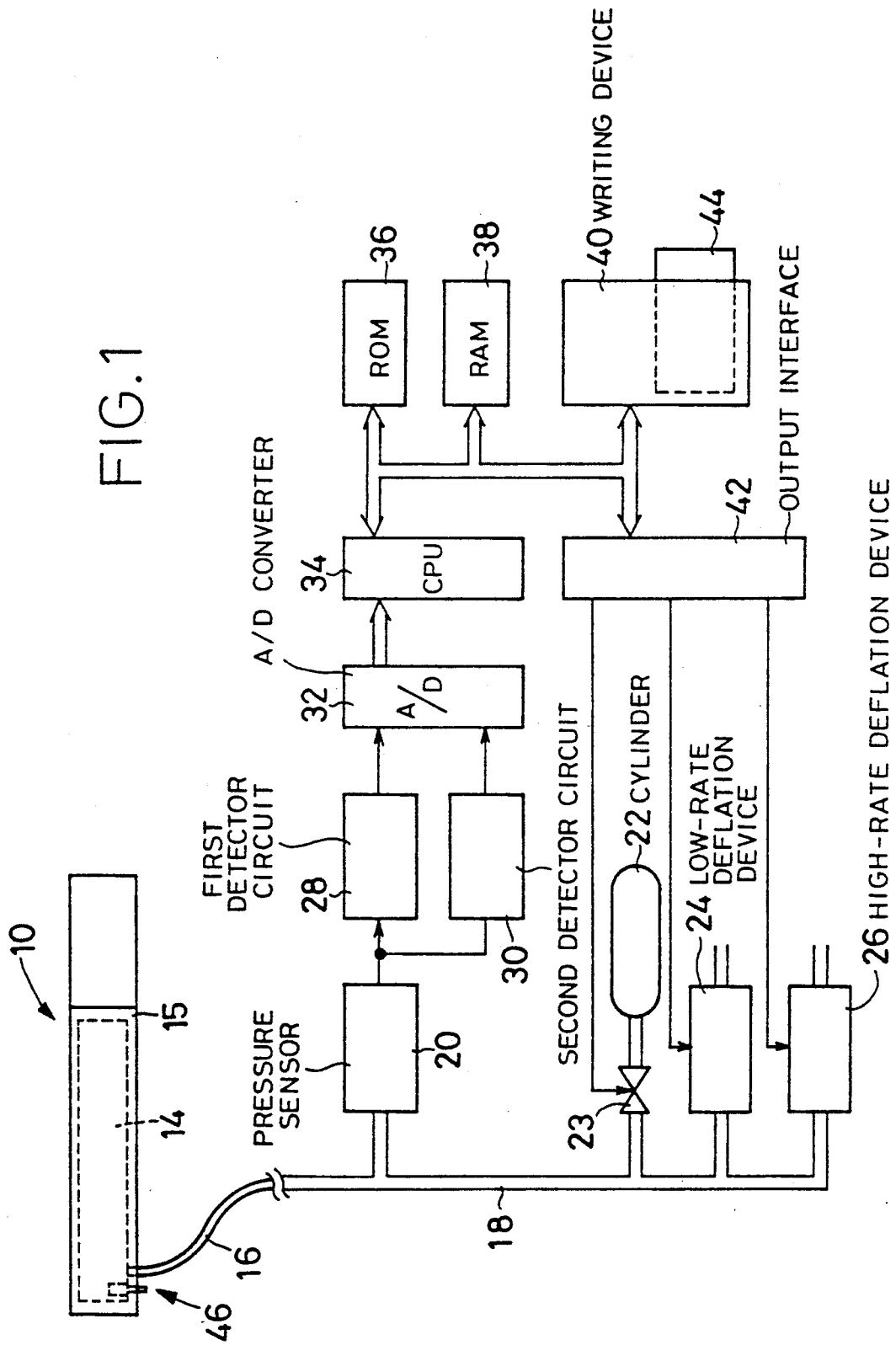
FIG. 1 is an illustrative view of the circuit diagram of the portable blood pressure monitoring system embodying the present invention.

Referring first to FIG. 1 there is diagrammatically shown a portable blood pressure monitoring system embodying the present invention. In the FIGURE reference numeral 10 designates a pressing device which is set around an upper arm or the like of a living body. The pressing device 10 includes an inflatable enclosure or cuff 14 of rubber which defines an inflatable pressure chamber 12 (see FIG. 2) therein, and a fabric bag 15 which accommodates the inflatable cuff 14 therein. The inflatable cuff 14 is connected to the main body of the monitoring system via a flexible piping in the form of a hose 16, the main body being interpreted to include all the members shown in FIG. 1 except for the cuff 14 and the hose 16. More specifically described, the cuff 14 is connected to a pressure sensor 20, a cylinder 22 containing compressed gas therein, a solenoid valve 23 for opening and closing the cylinder 22, a low-rate deflation device 24 and a high-rate deflation device 26 via piping 18 in the main body. The pressure sensor 20 supplies a pressure signal SP representative of variation in fluid pressure in the pressure chamber 12, to a first and a second detector circuit 28, 30. The first detector circuit 28 includes a low-pass filter and, upon reception of pressure signal SP, supplies a cuff-pressure signal SK representative of variation in static pressure of the fluid pressure in the pressure chamber 12, to a central processing unit (CPU) 34 via an analog/digital (A/D) converter 32. Meanwhile, the second detector circuit 30 includes a band-pass filter and, upon reception of pressure signal SP, supplies a pulse-wave signal SM representative of pulse waves applied to the cuff 14, to the CPU 34 via the A/D converter 32. The pulse waves are oscillatory pressure waves produced from an arterial vessel running beneath the pressing device 10, in synchronization with pulsation of the heart of the subject.

The CPU 34 is coupled via data bus to a read-only memory (ROM) 36, a random access memory (RAM) 38, a writing device 40 and an output interface 42, and processes signals according to software programs prestored in the ROM 36 by utilizing the temporary-storage function of the RAM 38. The CPU 34 controls the operations of the solenoid valve 23 and the low- and high-rate deflation devices 24, 26 via the output interface 42 so as to effect a blood pressure measurement on the subject. Further, the CPU 34 operates to determine a blood pressure of the subject based on pulse-wave signal SM and cuff-pressure signal SK, and commands the writing device 40 to write data indicative of the determined blood pressure together with the current time, on a memory card 44. The more detailed description of the blood pressure measurement is omitted since such description is not very important in understanding the present invention.

Figure 2:
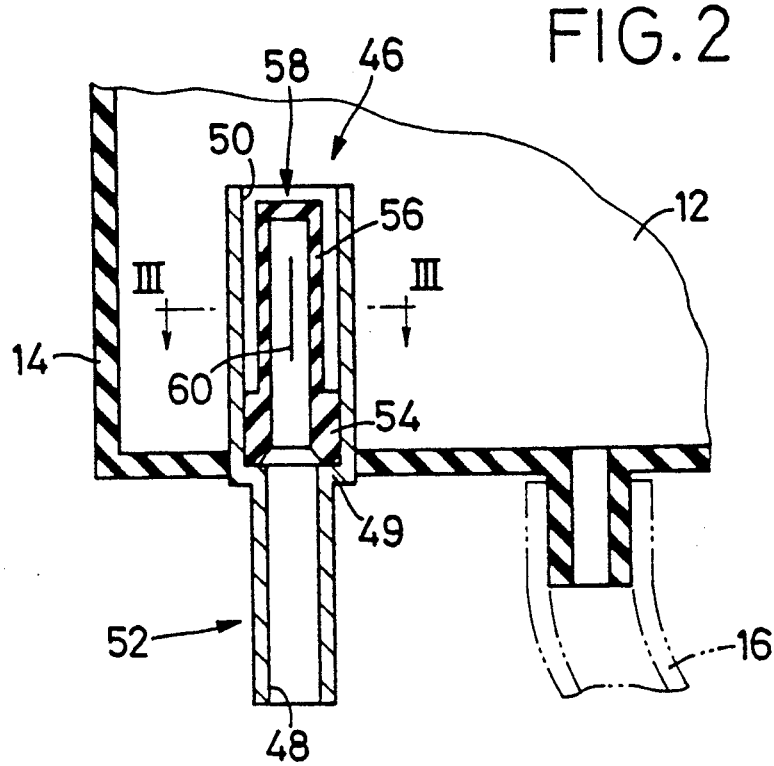
FIG. 2 is an enlarged view in cross section partially showing an inflatable cuff of the monitoring system of FIG. 1.

As clearly shown in FIG. 2, the pressure chamber 12 is provided with a relief-valve device 46. The relief-valve device 46 includes a fixture member 52 and a valve member 58. The fixture member 52 has a stepped cylindrical shape including a small-diameter portion 48 and a large-diameter portion 50 connected to each other at an intermediate shoulder portion 49 thereof. The valve member 58 is formed of rubber and has a generally cylindrical shape, one of opposite axial ends thereof being closed and the other end being open. The valve member 58 includes, on the open-end side thereof, a large-diameter portion 54 whose outer diameter is slightly larger than an inner diameter of the large-diameter portion 50 of the fixture member 52 and is sufficiently larger than an outer diameter of the remaining, small-diameter portion 56 of the valve member 58. The fixture member 52 is fluid-tightly secured to the inflatable cuff 14 such that the small-diameter portion 48 is exposed to the atmosphere while the large-diameter portion 50 is located in the pressure chamber 12. The valve member 58 is press fitted in the large-diameter portion 50 of the fixture member 52 such that the large-diameter portion 54 of the valve member 58 is in fluid-tight contact with the shoulder portion 49 of the fixture member 52. Thus, it needs a predetermined drag force to draw the valve member 58 out of the fixture member 52.

Figure 3:
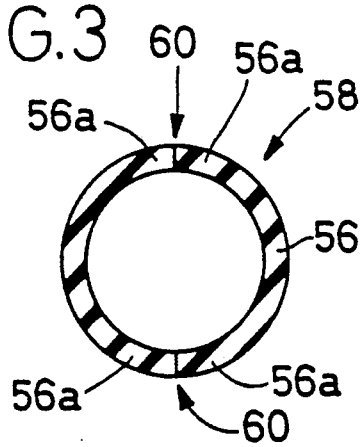
FIG. 3 is an enlarged cross-sectional view of a valve member of a relief-valve device of the monitoring system of FIG. 1, placed in an inoperative condition thereof, taken along line III—III of FIG. 1.
Figure 4:
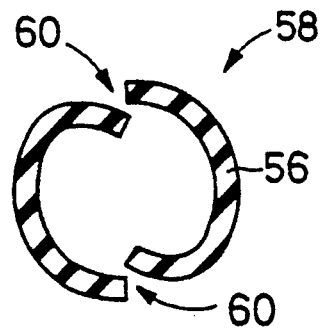
FIG. 4 is a view corresponding to FIG. 3, showing the valve member in an operative condition thereof in which the valve member permits the pressurized fluid in the inflatable cuff to be discharged therethrough.

The small-diameter portion 56 of the valve member 58 has a pair of opposite cuts 60 of a predetermined length made through the thickness of the cylindrical side wall of the small-diameter portion 56. The cuts 60 extend axially of the valve member 58, namely, in parallel to the longitudinal axis of the valve member 58. These cuts 60 normally are closed in a fluid-tight manner, as shown in FIG. 3. Meanwhile, if the fluid pressure in the pressure chamber 12, accordingly, pressure applied to the outer circumferential surface of the small-diameter portion 56 of the valve member 58, exceeds a predetermined value, the cuts 60 are opened such that one of a pair of lips 56a, 56a adjacent to each cut 60 is more largely elastically deformed radially inwardly than the other lip, as shown in FIG. 4. The hardness, diameter, thickness and other parameters of the small-diameter portion 56 of the valve member 58 are predetermined to exhibit the above-indicated effect.

There will be described the operation of the relief-valve device 56 constructed as described above.

Initially, pressurized gas is supplied from the cylinder 22 to the pressure chamber 12 of the cuff 14 via the piping 18 and the hose 16, so as to inflate the pressure chamber 12 and thereby increase fluid pressure in the pressure chamber 12 up to 180 mmHg, for example. In this situation, the cuts 60 of the valve member 58 are fluid-tightly closed as shown in FIG. 3. Meanwhile, if the fluid pressure in the pressure chamber 12 exceeds the predetermined value, for example 350 mmHg, due to a failure caused in the main body of the monitoring system, the relief-valve device 46 is placed in an operative position thereof in which the cuts 60 of the small-diameter portion 56 are opened such that one of the pair of lips 56a, 56a adjacent to each cut 60 is largely deformed radially inwardly of the small-diameter portion 56 (or valve member 58). As a result, the pressure chamber 12 is brought into fluid communication with the atmosphere via the relief-valve device 46 in the operative position, and the pressurized fluid in the pressure chamber 12 is discharged into the atmosphere and the fluid pressure in the pressure chamber 12 is decreased.

A test using a valve member having a hardness of 65 degree (according to the testing method of JIS (Japanese Industrial Standard)—K 6301), a small-diameter portion of 4 mm outer diameter and 0.75 mm thickness and a pair of cuts of 6 mm length, showed that the fluid pressure in the pressure chamber 12 was decreased to about 20 mmHg as a result of the discharge of the pressurized fluid from the pressure chamber 12, though the supply of the pressurized fluid from the cylinder 22 to the pressure chamber 12 had been continued.

Figure 5:
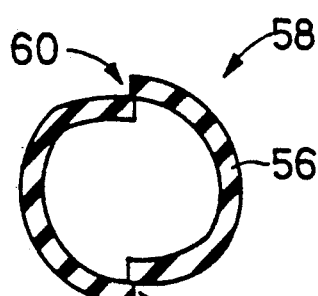
FIG. 5 is a view corresponding to FIG. 3, showing the valve member in the operative condition thereof after the pressurized fluid in the inflatable cuff has been discharged therethrough.
Figure 6:
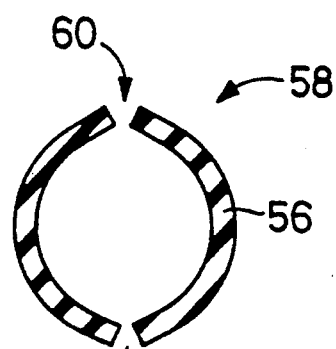
FIG. 6 is a view corresponding to FIG. 3, showing the valve member in a temporary condition thereof when the valve member is restored from the operative condition of FIG. 5 to the inoperative condition of FIG. 3.

Even after the pressurized fluid in the pressure chamber 12 has been discharged into the atmosphere and the fluid pressure of the pressure chamber 12 has been decreased to the minimum level, the valve member 58 continues to be in a condition thereof as shown in FIG. 5 in which the pair of lips 56a, 56a adjacent to each cut 60 overlap each other in the radial direction of the small-diameter portion 56. With the valve member 58 being in this condition, it is not permitted to increase the fluid pressure in the pressure chamber 12. An air-blowing device (not shown) is used to blow air into the valve member 58 from the small-diameter portion 48 of the fixture member 52, so as to release the overlapping of the pair of lips 56a, 56a as shown in FIG. 6 and thereby restore the valve member 58 to the condition shown in FIG. 3, namely restore the relief-valve device 46 to the inoperation position thereof.

In the illustrated embodiment, the relief-valve device 46 for preventing an excessively high fluid pressure in the pressure chamber 12, is directly associated with the pressure chamber 12 of the pressing device 10, in contrast to the conventional apparatus in which the relief-valve device is disposed on the upstream side of the flexible hose regarding the pressurized fluid fed from the main body of the apparatus to the pressure chamber via the hose. Therefore, the relief-valve device 46 of the present monitoring system is operated directly depending on the level of the fluid pressure in the pressure chamber 12. Accordingly, the present BP monitoring system is free from a problem that the relief-valve device 46 erroneously is operated due to bending of the flexible hose 16, thereby eliminating the trouble of restoring the relief-valve device 46 to its inoperative position. Since, in the present portable system, the flexible hose 16 is normally held inside the clothes of the subject and likely is bent double inside the clothes, the above-indicated advantage is more significant.

In the instant embodiment the rubber valve member 58 having the axial cuts 60 in the small-diameter cylindrical portion 56 thereof, serves as a valve mechanism for relieving the pressurized fluid in the pressure chamber 12 into the atmosphere. This valve mechanism is not operated, namely, not changed from the inoperative position in which the pair of lips 56a, 56a adjacent to each cut 60 are in fluid-tight contact with each other, to the operative position, until the fluid pressure in the pressure chamber 12 is increased up to a comparatively high level such as 350 mmHg. However, in the operative position of the valve mechanism, one of the pair of lips 56a, 56a is largely deformed radially inwardly and the lips 56a, 56a overlap each other in the radial direction of the small-diameter portion 56. Consequently, the valve mechanism is not automatically restored from the operative position to the inoperative position even if the pressure level in the pressure chamber 12 is lowered to a comparatively low level. As described above, even with the pressurized fluid being supplied from the cylinder 22 to the pressure chamber 12, the valve mechanism in the operative position permits the fluid pressure in the pressure chamber 12 to be reduced to a sufficiently low level such as about 20 mmHg. The valve mechanism or relief-valve device 46 of the present monitoring system is simple in construction and is constituted by the least number of parts. The valve mechanism serves to avoid an unnecessary, excessively high pressure applied to the subject.

While in the illustrated embodiment the fixture member 52 is used to secure the valve member 58 to the cuff 14, it is possible to directly secure the valve member (58) to the cuff (14). In this case, it is preferred that the valve member (58) be formed integral with the cuff (14).

Although in the illustrated embodiment the two cuts 60 are used, it is possible to make and use a single cut (60).

The relief-valve device 46 consisting of the fixture member 52 and the valve member 58 may be substituted for by other types of relief means.

While in the illustrated embodiment the rubber cuff 14 is used as the means for defining the inflatable pressure chamber, it is possible to employ, in place of the rubber cuff 14, a pair of superimposed vinyl sheets adhered to each other at the peripheral portions thereof and defining an inflatable pressure chamber therein.

Although the illustrated BP monitoring system is of the portable type, it is possible to apply the principle of the present invention to other BP measuring apparatus which is adapted to feed pressurized fluid from a main body thereof to an inflatable pressure chamber via a flexible piping.

While the present invention has been described with particularities for illustrative purposes only, it is to be understood that the present invention may be embodied with various changes, improvements and modifications that may occur to those skilled in the art without departing from the scope and spirit of the invention defined in the appended claims.

What is claimed is:

1. An apparatus for automatically measuring a blood pressure of a subject, comprising:
    means for defining an inflatable pressure chamber, said means being adapted to be set on a body portion of said subject;
    a flexible piping;
    means for supplying a pressurized fluid to said inflatable pressure chamber via said flexible piping so as to increase fluid pressure in the pressure chamber and thereby press said body portion of the subject; and
    relief means for, if said fluid pressure in said inflatable pressure chamber exceeds a predetermined value, discharging the pressurized fluid in said inflatable pressure chamber, into atmosphere, so as to decrease said fluid pressure, the relief means being supported by said means for defining the pressure chamber;
    said relief means comprising a cylindrical valve member formed of an elastically deformable material and having a pair of opposite axial ends one of which is a closed end and the other of which is an open end, said open end communicating with said atmosphere, said valve member including a cylindrical side wall and at least one axial cut of a predetermined length formed through said side wall, said valve member being, while said fluid pressure in the pressure chamber is below said predetermined value, in an inoperative position thereof in which said at least one cut is fluid-tightly closed, said valve member being placed, when said fluid pressure in the pressure chamber exceeds said predetermined value, in an operative position thereof in which said at least one cut is opened due to elastic deformation of one of a pair of lips adjacent to said at least one cut so that the pressurized fluid in the pressure chamber is discharged into said atmosphere through the opened cut and said fluid pressure in the pressure chamber is decreased.

2. The apparatus as set forth in claim 1, further comprising
    means for detecting pulse waves produced from an artery running beneath said body portion of the subject, and
    means for determining a blood pressure of the subject based on the detected pulse waves.

3. The apparatus as set forth in claim 1, wherein said cylindrical valve member is formed of a rubber material.

4. The apparatus as set forth in claim 1, wherein said at least one cut consists of a pair of opposite cuts made in the cylindrical side wall of said cylindrical valve member.

5. The apparatus as set forth in claim 3, wherein said means for defining said inflatable pressure chamber comprises an inflatable cuff formed of a rubber material, said cylindrical valve member being formed integral with said inflatable cuff such that the open end of the valve member is exposed to said atmosphere and the closed end thereof is located in the pressure chamber.

6. The apparatus as set forth in claim 3, wherein said at least one cut is opened when the fluid pressure in said inflatable pressure chamber exceeds 350 mmHg.

7. The apparatus as set forth in claim 3, wherein said cylindrical valve member is restored from said operative position thereof to said inoperative position thereof by blowing air into a cylindrical main body of the valve member through the open end thereof.

8. The apparatus as set forth in claim 3, wherein said cylindrical valve member once placed in said operative position thereof continues to be in the operative position due to radial overlapping of said pair of lips adjacent to the opened at least one cut, thereby permitting the pressurized fluid in said inflatable pressure chamber to be discharged through the opened at least one cut, even if the supply means continues to supply the pressurized fluid to the pressure chamber.

9. The apparatus as set forth in claim 8, wherein the fluid pressure in said inflatable pressure chamber is decreased down to about 20 mmHg while said cylindrical valve member continues to be in said operative position thereof.

10. A pressing device for pressing a body portion of a subject, comprising:
    means for defining an inflatable pressure chamber, said means being adapted to be set on said body portion of said subject;
    means for supplying a pressurized fluid to said inflatable pressure chamber so as to increase fluid pressure in the pressure chamber and thereby press said body portion of said subject; and
    relief means for, if said fluid pressure in said inflatable pressure chamber exceeds a predetermined value, discharging the pressurized fluid in said inflatable pressure chamber, into atmosphere, so as to decrease said fluid pressure, the relief means being supported by said means for defining the pressure chamber;

said relief means comprising a cylindrical valve member formed of an elastically deformable material and having a pair of opposite axial ends one of which is a closed end and the other of which is an open end, said open end communicating with said atmosphere, said valve member including a cylindrical side wall and at least one axial cut of a predetermined length formed through said side wall, said valve member being, while said fluid pressure in the pressure chamber is below said predetermined value, in an inoperative position thereof in which said at least one cut is fluid-tightly closed, said valve member being placed, when said fluid pressure in the pressure chamber exceeds said predetermined value, in an operative position thereof in which said at least one cut is opened due to elastic deformation of one of a pair of lips adjacent to said at least one cut so that the pressurized fluid in the pressure chamber is discharged into said atmosphere through the opened cut and said fluid pressure in the pressure chamber is decreased.

11. The device as set forth in claim 10, further comprising a flexible piping, wherein the supply means supplies the pressurized fluid to said inflatable pressure chamber via said flexible piping.

12. The device as set forth in claim 4, wherein said cylindrical valve member is formed of a rubber material.

13. The device as set forth in claim 10, wherein said means for defining the pressure chamber comprises an inflatable cuff formed of an elastically deformable material, said relief means further comprising a fixture member fluid-tightly secured to said cuff, said fixture member having a stepped cylindrical shape including a small-diameter portion, a large-diameter portion, and a stepped portion connecting said small and large-diameter portions to each other, said small-diameter portion being exposed to said atmosphere, while said large-diameter portion is located in said pressure chamber;

said valve member further including a large-diameter cylindrical portion extending axially outwardly from said open end of the valve member and having an outer diameter of a cylindrical main body of the valve member and slightly smaller than an inner diameter of said large-diameter portion of said fixture member, said valve member being press-fitted in said large-diameter portion of said fixture member such that said large-diameter cylindrical portion of said valve member is held in fluid-tight contact with said stepped portion of said fixture member and communicates with said small-diameter portion of said fixture member.

14. The device as set forth in claim 10, wherein a second cut diametrically opposite said at least one cut is formed through said cylindrical side wall of the valve member.

15. The device as set forth in claim 10, wherein said valve member once placed in said operative position continues to be in the operative position due to radial overlapping of said pair of lips, thereby permitting the pressurized fluid in said pressure chamber to be discharged through said opened cut, even if the supply means continues to supply the pressurized fluid to the pressure chamber.

16. The device as set forth in claim 10, wherein said valve member is restored from said operative position to said inoperative position by blowing air into a cylindrical main body of the valve member through said open end of the valve member.

17. An apparatus for automatically measuring a blood pressure of a subject, comprising:

an inflatable cuff formed of a rubber material and having an inflatable pressure chamber, said cuff being adapted to be set on a body portion of said subject;

a flexible piping;

means for supplying a pressurized fluid to said pressure chamber via said piping so as to increase fluid pressure in the pressure chamber and thereby press said body portion of the subject;

relief means for discharging the pressurized fluid in said pressure chamber, into atmosphere, if said fluid pressure in the pressure chamber exceeds a predetermined value;

said relief means comprising a fixture member fluid-tightly secured to said cuff, said fixture member having a stepped cylindrical shape including a small-diameter portion, a large-diameter portion, and a stepped portion connecting said small and large-diameter portions to each other, said small-diameter portion being exposed to said atmosphere, while said large-diameter portion is located in said pressure chamber;

said relief means further comprising a cylindrical valve member formed of a rubber material and having a pair of opposite axial ends one of which is a closed end and the other of which is an open end, said valve member including a cylindrical main body and at least one axial cut of a predetermined length formed through said cylindrical main body, said valve member further including a large-diameter cylindrical portion extending axially outwardly from said open end of the valve member and having an outer diameter sufficiently larger than an outer diameter of said main body of the valve member and slightly smaller than an inner diameter of said large-diameter portion of said fixture member, said valve member being press-fitted in said large-diameter portion of said fixture member such that said large-diameter cylindrical portion of said valve member is held in fluid-tight contact with said stepped portion of said fixture member and communicates with said small-diameter portion of said fixture member; and said valve member being, while said fluid pressure in the pressure chamber is below said predetermined value, in an inoperative position thereof in which said at least one cut is fluid-tightly closed, said valve member being placed, when said fluid pressure in the pressure chamber exceeds said predetermined value, in an operative position thereof in which said at least one cut is opened due to elastic deformation of one of a pair of lips adjacent to said at least one cut so that the pressurized fluid in the pressure chamber is discharged into said atmosphere through the opened cut.

18. The apparatus as set forth in claim 17, further comprising means for detecting a pulse wave produced from an arterial vessel lying under said body portion of the subject, and means for determining a blood pressure of the subject based on the detected pulse wave.

19. The apparatus as set forth in claim 17, wherein a second cut opposite said at least one cut is formed through said cylindrical main body of the valve member.

20. The apparatus as set forth in claim 17, wherein said valve member once placed in said operative position continues to be in the operative position due to radial overlapping of said pair of lips, thereby permitting the pressurized fluid in said pressure chamber to be discharged through said opened cut, even if the supply means continues to supply the pressurized fluid to the pressure chamber.

21. The apparatus as set forth in claim 17, wherein said valve member is restored from said operative position to said inoperative position by blowing air into said cylindrical main body of the valve member through said open end of the valve member.

* * * * *